(12) United States Patent
Muradyan

(10) Patent No.: US 10,055,836 B1
(45) Date of Patent: Aug. 21, 2018

(54) AUTOMATED METHOD FOR TISSUE-BASED CONTRAST MEDIA ARRIVAL DETECTION FOR DYNAMIC CONTRAST ENHANCED MRI

(71) Applicant: iCAD, Inc., Nashua, NH (US)

(72) Inventor: Naira Muradyan, Bathesda, MD (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 358 days.

(21) Appl. No.: 14/497,478

(22) Filed: Sep. 26, 2014

(51) Int. Cl.
G06T 7/00 (2017.01)
G06K 9/46 (2006.01)
A61B 5/055 (2006.01)

(52) U.S. Cl.
CPC ............ G06T 7/0012 (2013.01); A61B 5/055 (2013.01); G06K 9/46 (2013.01)

(58) Field of Classification Search
CPC .......... G06T 7/0012; G06K 9/46; A61B 5/055
See application file for complete search history.

(56) References Cited

U.S. PATENT DOCUMENTS

| | | | |
|---|---|---|---|
| 6,584,216 B1 | 6/2003 | Nyul et al. | |
| 6,597,937 B2 | 7/2003 | Liu et al. | |
| 6,647,283 B2 | 11/2003 | Klotz | |
| 7,233,687 B2 | 6/2007 | Ashton | |
| 7,333,845 B2 | 2/2008 | Hundley et al. | |
| 7,346,202 B1 | 3/2008 | Schneider | |
| 7,583,992 B2 | 9/2009 | Mistretta et al. | |
| 7,587,077 B2 | 9/2009 | Schneider | |
| 7,768,652 B2 | 8/2010 | Everett | |
| 7,903,853 B2 | 3/2011 | Muradyan et al. | |
| 8,180,126 B2 | 5/2012 | Safdar et al. | |
| 8,326,400 B2 | 12/2012 | Taxt et al. | |
| 8,848,998 B1 | 9/2014 | Muradyan | |
| 2007/0165927 A1* | 7/2007 | Muradyan | G06K 9/40 382/128 |
| 2007/0216909 A1 | 9/2007 | Everett et al. | |
| 2008/0304728 A1 | 12/2008 | Licato et al. | |
| 2009/0046908 A1 | 2/2009 | Safdar et al. | |
| 2009/0190806 A1 | 7/2009 | Muradyan et al. | |
| 2010/0128946 A1 | 5/2010 | Fidrich et al. | |

(Continued)

OTHER PUBLICATIONS

Verma, Sadhna, et al. "Overview of dynamic contrast-enhanced MRI in prostate cancer diagnosis and management." American Journal of Roentgenology 198.6 (2012): 1277-1288.*

(Continued)

*Primary Examiner* — Bhavesh Mehta
*Assistant Examiner* — Menatoallah Youssef

(57) ABSTRACT

A system and method for automated contrast arrival detection in temporally phased images or datasets of tissues effectively determines contrast arrival in regions that are substantially free of arteries. A plurality of tissue voxels in a plurality of temporally phased images are identified as a function of voxel enhancement characteristics associated with discrete tissue voxels. A processor/process computes average enhancement characteristics from the plurality of identified tissue voxels. The average enhancement characteristics are compared with predetermined average enhancement characteristics associated with contrast media arrival phases. Contrast media arrival phases in the temporally phased images are provided based on the comparison.

10 Claims, 6 Drawing Sheets

(56) References Cited

U.S. PATENT DOCUMENTS

| | | |
|---|---|---|
| 2011/0194746 A1 | 8/2011 | Riederer |
| 2011/0206250 A1 | 8/2011 | McGinnis et al. |
| 2014/0163403 A1* | 6/2014 | Lenox ............... A61B 5/026 |
| | | 600/504 |

OTHER PUBLICATIONS erma (Verma, Sadhna, et al. "Overview of dynamic contrast-enhanced MRI in prostate cancer diagnosis and management." American Journal of Roentgenology 198.6 (2012): 1277-1288.).*
Hendrick, "Breast MRI: Fundamentals and Technical Aspects", 2008, Publisher: Springer, Published in: US.
Pratt, "Digital Image Processing: PIKS Scientific Inside, 4TH Ed." 2007, p. 277 Publisher: John Wiley & Sons, Inc., Published in: US.
Oppenheim, et al., "Discrete-Time Signal Processing", 1999, pp. 468-471, Publisher: Prentice Hall, Published in: US.
Rijpkema, et al., "Method for Quantitative Mapping of Dynamic MRI Contrast Agent Uptake in Human Tumors", "Journal of Magnetic Resonance Imaging", 2001, pp. 457-463, vol. 14, Publisher: Wiley-Liss, Inc., Published in: US.

* cited by examiner

AUTOMATED METHOD FOR TISSUE-BASED CONTRAST MEDIA ARRIVAL DETECTION FOR DYNAMIC CONTRAST ENHANCED MRI

FIELD OF THE INVENTION

This application relates generally to the processing of time-resolved medical images, during the acquisition of which a signal-enhancing contrast media is administered. More particularly, this application relates to techniques for detecting the arrival of signal-enhancing contrast media in time-resolved medical images.

BACKGROUND OF THE INVENTION

Early detection of disease or malignant tissue can lead to a better prognosis. The development of non-invasive methods for detection and characterization of tumors and other anomalies has an extreme importance in current medicine. Dynamic, contrast-enhanced imaging provides an effective means of monitoring non-invasively and with high spatial and/or temporal resolutions the microvascular properties of tumors and tissues. The increased permeability of tumor vasculature gives rise to increased leakage of tracers including contrast agents, and enables characterization of enhancement patterns in the tissue. One method for characterization of tumor microvasculature is dynamic, contrast-enhanced (DCE) magnetic resonance imaging (MRI), or DCE-MRI. For DCE-MRI, multi-slice images are typically acquired before, during, and after the contrast agent infusion, resulting in the acquisition of a time sequence of image volumes, also referred to as a dynamic, contrast-enhanced image dataset.

Dynamic, contrast-enhanced image datasets can be postprocessed using image analysis software to create supplemental data for interpretation by a radiologist. Such data can illustrate diagnostically important criterion that can not be evident from the original grayscale images. Examples of such supplemental data can include parametric maps, time-enhancement curve shape estimations, and/or multi-parametric analysis results. Some examples of image post-processing analysis techniques for creating such supplemental data can be seen in *Breast MRI: Fundamentals and Technical Aspects,* Hendrick, R. Edward, 2008, XVI, pp. 171-186 and U.S. Published Patent Application No. 2009/0190806, entitled "METHOD FOR TRACKING OF CONTRAST ENHANCEMENT PATTERN FOR PHARMACOKINETIC AND PARAMETRIC ANALYSIS IN FAST-ENHANCING TISSUES USING HIGH-RESOLUTION MRI," the contents of which are fully incorporated herein by way of useful background information.

Many image post-processing analysis techniques require identification of the arrival of contrast media administrated via the arterial/capillary system to the organ/tissue of interest. Contrast media arrival can vary widely depending on multiple factors, such as the speed and site of injection, location of organ/tissue in the body, patient blood flow patterns, etc. In many DCE image post-processing analyses, the time moment when contrast media concentration (and therefore, image signal intensity) achieves peak in major blood vessels or arteries close to the tissue/organ of interest signifies a key time point in a time array to be used for image post-processing analysis. In such cases, correct identification of contrast media arrival is required to generate correct diagnostic interpretation data.

Applicant's commonly assigned, co-pending U.S. patent application Ser. No. 12/797,934, entitled AUTOMATED CONTRAST MEDIA ARRIVAL DETECTION METHOD FOR DYNAMIC CONTRAST ENHANCED MRI, by Naira Muradyan—the teachings of which are incorporated herein by reference as useful background information—discloses automated methods suitable for detecting contrast arrival in various tissues, such as breasts, lungs or prostates. However, such methods rely on the presence of large vessels within the field of view in order to detect the arrival event. Methods disclosed in the '934 application are inaccurate for detecting arrival when executed on image datasets lacking such features. Examples of tissues that may lack such features include upper brain structures, hands and/or fingers, feet, unilateral or bilateral breast with limited imaging field (e.g., excludes aorta), prostate or female pelvis (cervix, uterus) with smaller imaging field (e.g., excludes iliac arteries), or unilateral lung with imaging field that excludes the aorta.

SUMMARY OF THE INVENTION

This invention enables automated contrast arrival detection in temporally phased images or datasets of tissues. The automated system and method are particularly suited for detection in images free from large vessels (e.g., arteries), though they reliably detect contrast arrival in images that contain such features as well. The automated system and method reliably detect contrast media arrival by identifying a plurality of tissue voxels in temporally phased images as a function of predetermined enhancement characteristics associated with individual tissue voxels, computing average enhancement characteristics from the plurality of identified tissue voxels, comparing the average enhancement characteristics with predetermined average enhancement characteristics associated with contrast media arrival phases, and identifying contrast media arrival phases in the temporally phased images based on the comparing.

In an illustrative embodiment a system and method provides a system and method for automated contrast arrival detection in temporally phased images or datasets of tissues effectively determines contrast arrival in regions that are substantially free of arteries. A plurality of tissue voxels in a plurality of temporally phased images are identified (and/or sets of identified tissue voxels are provided) as a function of voxel enhancement characteristics associated with discrete tissue voxels. A processor/process computes average enhancement characteristics from the plurality of identified tissue voxels. The average enhancement characteristics are compared using a comparator/comparison function/process/processor with predetermined average enhancement characteristics associated with contrast media arrival phases. Contrast media arrival phases in the temporally phased images are provided based on the comparison. Illustratively, the system and method can establish a plurality of candidate arrival phases and determine if an average signal enhancement curve after the candidate phase fits under the a gradient line of average signal enhancement change at a first candidate arrival phase from the plurality of candidate arrival phases; and if the first signal enhancement curve does not fit, the system can select a next candidate arrival phase from the plurality of candidate arrival phases. If the first signal enhancement curve fits, the system and method can select the candidate arrival phase as one of the contrast media arrival phases in at least one of the datasets. The system and method can store at least one of the contrast media arrival phases in a data storage device. The system and method can output at least one of the contrast media arrival phases to an output device, such as a printer display, networked device (e.g. a laptop, tablet, smart phone, etc.). Illustratively, the tissues are substantially free of arteries. The identification of the tissue voxels can include comparing voxel enhancement values of the temporally phased images with an intensity noise threshold and identifying the plurality of tissue voxels based at least on the comparing process. Alternatively, the identification can include comparing signal intensity enhancement voxel values of the temporally phased images with a signal intensity enhancement threshold. As a further alternative, the identification can include comparing signal intensity madness voxel values of the temporally phased images with a smoothness threshold. Additionally, the comparison function/process/processor can include eliminating a dynamic phase from consideration as the contrast arrival phase if the average signal intensity of the dynamic phase exceeds at least one average signal intensity of a later dynamic phase.

In a further illustrative embodiment, a system and method for automated contrast arrival detection in temporally phased images or datasets of tissues includes identification of/sets of identified tissue voxels in a plurality of the temporally phased images as a function of predetermined enhancement characteristics associated with discrete tissue voxels that include baseline signal intensity values and late phase signal intensity values to derive a signal intensity enhancement value for each of the voxels. A comparison/comparator function/process/processor compares the signal intensity enhancement value to a signal intensity enhancement threshold. A plurality of candidate arrival phases are thereby established/provided based upon the comparison; and contrast media arrival phases in the temporally phased images are identified based upon the establishment of such candidates.

In another illustrative embodiment, a system and method for automated contrast arrival detection in temporally phased images or datasets of tissues includes identification of/sets of identified tissue voxels in a plurality of the temporally phased images as a function of predetermined enhancement characteristics associated with discrete tissue voxels. A processor/process computes signal intensity curve madness for the identified tissue voxels. A comparison/comparator function/process/processor compares signal curve madness to a smoothness threshold. Based upon this comparison, contrast media arrival phases are identified/provided in the temporally phased images.

BRIEF DESCRIPTION OF THE DRAWINGS

The invention description below refers to the accompanying drawings, of which.

DETAILED DESCRIPTION

In the present disclosure, the terms "pixels" and "voxels" can be used interchangeably to refer to an element in an image. Image data is generally represented in units of picture elements (pixels). A pixel generally refers to the information stored for a single grid in an image or a basic unit of the composition of an image, usually in a two-dimensional space, for example, x-y coordinate system. Pixels can become volumetric pixels or "voxels" in three-dimensional space (x, y, z coordinates) by the addition of at least a third dimension, often specified as a z-coordinate. A voxel thus refers to a unit of volume corresponding to the basic element in an image that corresponds to the unit of volume of the tissue being scanned. It should be appreciated that this disclosure can utilize pixels, voxels and any other unit representations of an image to achieve the desired objectives presented herein. Both pixels and voxels each contain a discrete intensity and/or color, which is typically defined as one or more digital values within a given range (for example, a grayscale intensity between 0 and 255, or discrete RGB values each between 0 and 255).

As used herein, the terms "dataset" or "image dataset" are employed interchangeably to refer to a plurality of images, a volume of images, a plurality of volumes, or even a plurality of datasets. By way of example, as introduced in the background of the disclosure, in dynamic, contrast-enhanced magnetic resonance imaging (DCE-MRI), a plurality of slice images is typically acquired before, during, and after contrast agent infusion, resulting in the acquisition of a time sequence of image volumes. In this imaging, "dataset" or "image dataset" are used to refer to a plurality of slice images of the tissue at a given time point, a plurality of slices images of the tissue across different time points, or a plurality of image volumes of the tissue across a plurality of discrete time points.

Figure 1:
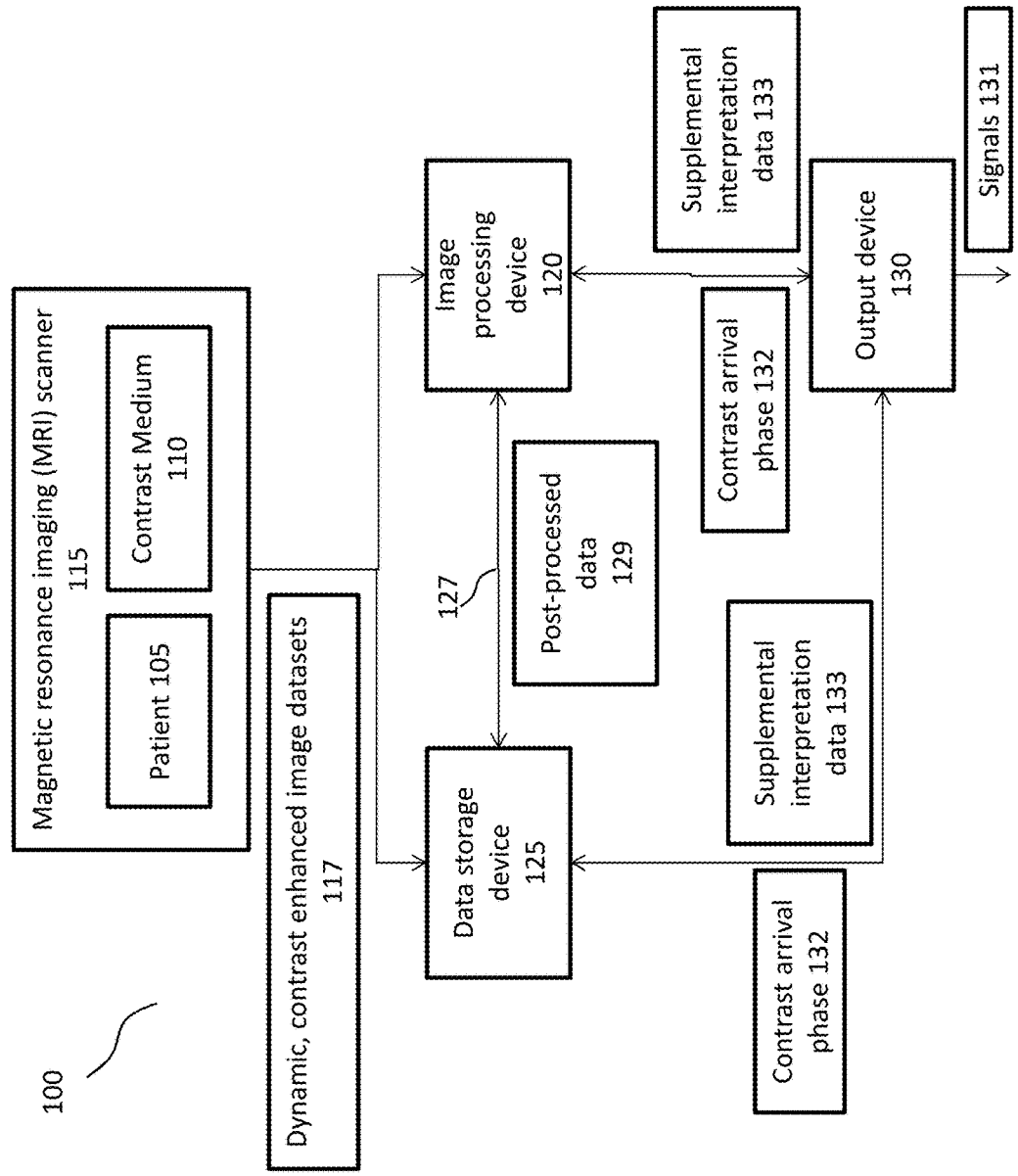
FIG. 1 is a block diagram of a medical examination system that employs an image processing device and corresponding image processing procedures in accordance with an illustrative embodiment.

With reference to FIG. 1, there is shown a block diagram of components of a medical examination system 100 according to an illustrative embodiment of this invention. The medical examination system can be utilized for assessing the health of a patient 105 by monitoring, using medical imaging technology, tissue of the patient before, during, and after the administration of a contrast medium 110. The contrast medium can be any media or agent useful in monitoring blood flow and/or tissue perfusion patterns such as, but not limited to, a gadolinium-based contrast agent. The contrast medium can be administered to the patient by intravenous injection, or another suitable infusion technique.

A magnetic resonance imaging (MRI) scanner 115 can be utilized for acquiring static anatomical or functional datasets, such as dynamic contrast-enhanced image datasets 117 of tissues using conventional or novel magnetic resonance imaging techniques. Alternatively, other dynamic image acquisition techniques can be used, in which case scanners employing different imaging technology such as, but not limited to, computed tomography (CT) scanners can be implemented as the image acquisition component of the medical examination system 100. In general, the results of such scanning include a stream of discrete image datasets (typically contrast-enhanced) acquired at predetermined time intervals defined by "dynamic" or "temporal" phases.

For purposes of this disclosure, the datasets include both the tissue to be monitored as well as nearby blood vessels (e.g., arteries), both of which are within the field of view.

The MRI scanner 115 can be coupled to an image processing device 120, such as a computer workstation, a computer server, or another device capable of performing image processing in accordance with an illustrative embodiment. The image processing device can include or comprise the console for controlling and acquiring images from the MRI scanner, where such console is capable of executing program instructions in the form of a computer-readable medium and/or contains hardware for carrying out the processes of the illustrative embodiment. Alternatively, the console can be deployed as part a device separate from the image processing device and operatively connected thereto by appropriate network interconnections. By way of one example (not shown in FIG. 1), the MRI scanner 115 can include or comprise the console and the dynamic, contrast-enhanced image datasets 117 acquired by the scanner can be transmitted via the console to the image processing device 120 for post-processing, which is described in further detail below.

The MRI scanner 115 can also be coupled to a data storage device 125 for storing the dynamic, contrast-enhanced image datasets 117. By way of one non-limiting example, the storage device can be a Picture Archiving and Communication System (PACS) for storing, retrieving, and distributing medical image data between components of the medical examination system 100. Alternatively, any directly attached or networked storage device with appropriate data organization can be employed to store, and allow retrieval of, the image datasets. For example, the storage device can comprise a removable disk or solid-state storage, a network-attached-storage appliance, a storage area network (SAN) and/or a remote data store accessed by a secure private network, such as a hospital wide area network or a public network. Appropriate layers of encryption can be applied to the transmitted as well as the stored data as required to satisfy various governmental and institutional security requirements. Such encryption techniques should be clear to those of ordinary skill.

In an embodiment, the image processing device 120 and the data storage device 125 are also coupled together (represented by a link 127). This can allow the data storage device to transmit the dynamic, contrast-enhanced image datasets 117 to be post-processed by the image processing device as needed. The image processing device can be further arranged to transmit the results of image post-processing in the form of post-processed data 129 to the storage device for storage for subsequent handling and use. Processes by which such information can be generated by the image processing device will be described in further detail herein below.

Another component of the medical examination system 100 is an output device 130 for outputting signals 131 associated with the dynamic, contrast-enhanced image datasets 117 and/or the post-processed data 129. The output device can comprise a printer, a computer monitor, a series of computer monitors, and/or other suitable signal output devices of conventional or novel design. The signals can be output in the form of raw image data or post-processed image data for visual inspection of the tissue. As shown, the output device might receive post-processed data information in the form of a contrast arrival phase 132 and supplemental image interpretation data 133 such as parametric color maps which, in an automated manner, allows the viewer to accurately visualize and interpret the behaviors of the enhancing tissue. Exemplary processes by which the image processing device 120 generates the data for display/reporting by the output device is now described in further detail.

It is expressly contemplated that components of the medical examination system 100 can connect to, and communicate with, each other via one or more of any type or combination of types of communication interfaces, including but not limited to physical interfaces, network interfaces, software interfaces, and the like. The communication can be by means of a physical connection, or can be wireless, optical, or by other means. Alternatively, image datasets can be transmitted indirectly by use of transportable storage devices (not shown in FIG. 1) such as but not limited to compact discs (CDs), digital video discs (DVDs), or solid state "flash" drives, in which case readers for said transportable storage devices can function as communication interfaces of the system.

Figure 2:
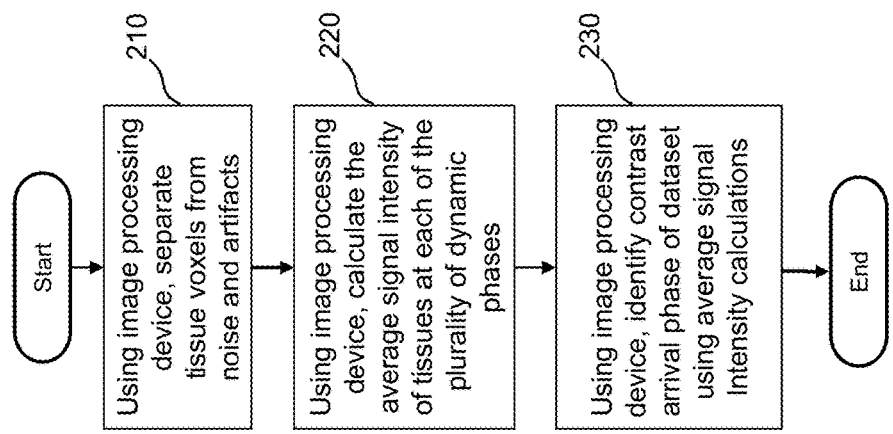
FIG. 2 is a runtime flow chart showing an illustrative automatic contrast arrival detection procedure that can be implemented in the medical examination system of FIG. 1.

With further reference to FIG. 2 and with continuing reference to FIG. 1, an automatic contrast arrival detection procedure or method 200 is now described in further detail.

Unlike contrast arrival detection methods described in above-incorporated U.S. patent application Ser. No. 12/797,934, method 200 is particularly suited for contrast arrival detection in image datasets in which arterial vessels do not appear within the three-dimensional field of view. Embodiments of anatomical regions in such image datasets can include upper brain structures, hands and/or fingers, feet, unilateral or bilateral breast with limited imaging field (e.g., excludes aorta), prostate or female pelvis (cervix, uterus) with smaller imaging field (e.g., excludes iliac arteries), or unilateral lung with imaging field (e.g., excludes aorta). If image acquisition devices image a prostate with less than 18 centimeters (cm) axial tissue coverage (i.e., only 18 cm of left to right anatomical coverage, centered on the prostate), the field of view will likely not include the major arteries, which will be outside the imaged anatomical area. Imaging prostatic tissue with such parameters can allow for better spatial resolution at the same temporal resolution, and thus is often preferred for diagnostic purposes.

The tissue-based automated contrast arrival detection systems and methods of the illustrative embodiments are also particularly suited for arrival detection in medical image datasets acquired using fast dynamic protocols. In one embodiment, methods can be performed on image datasets acquired with a temporal resolution of no more than 20 seconds per phase and preferably, on image datasets acquired with a temporal resolution of no more than 10 seconds/phase.

Reference is now made to FIG. 2, which illustrates an exemplary embodiment of a method 200 particularly suited for contrast arrival detection in image datasets described herein above. In some embodiments, the image processing device 120 can implement and execute method 200. In summary, method 200 detects contrast arrival by identifying the onset of enhancement using a substantial number of tissue voxels in input image datasets, as opposed to other arrival detection methods that identify the onset of enhancement in only specific vessel voxels (e.g., arteries) and/or only significantly enhancing tissue voxels. For example, during runtime operation, method 200 can utilize at least 20% of the voxels in a 3D image dataset, and preferably, can use at least 30% of the voxels. The actual percentage can vary, depending on the amount of tissue enhancement within the imaged field of view and the amount of noisy voxels that can be discarded by the methods described herein.

Referring now to step 210 of method 200, an image-processing device first separates tissue voxels from other noise and artifacts in an input image dataset. In one embodiment, the image-processing device can consider a tissue voxel any voxel in a dataset that has signal intensity enhancement characteristics meeting predefined rules; the device can discard any other voxel from further processing as a non-tissue voxel.

In an embodiment, the image-processing device can implement a rule at step 210 that pertains to the baseline or pre-contrast signal intensity value of a voxel as compared to a noise threshold. The device can derive a baseline signal intensity value for method 200 from any dynamic phase in the dataset prior to contrast agent administration or arrival in the field of view (referred to herein as a reference baseline phase). Alternatively, the device can derive the baseline signal intensity value from statistics of a plurality of reference baseline phases. The image-processing device can enable a user to manually set the noise threshold to be utilized in the rule or, alternatively, can derive the noise threshold automatically from the dataset using processing techniques described in the applicant's commonly assigned U.S. Pat. No. 7,903,853, entitled AUTOMATED METHODS FOR PRE-SELECTION OF VOXELS AND IMPLEMENTATION OF PHARMACOKINETIC AND PARAMETRIC ANALYSIS FOR DYNAMIC CONTRAST ENHANCED MRI AND CT, the teachings of which are incorporated by reference as useful background information. In an embodiment, the logic rule takes the form of: $I_v$(FirstBaseline)>IntensityNoiseThreshold, in which a voxel v is not discarded if its baseline signal intensity value as represented by $I_v$(FirstBaseline) is greater than the noise threshold represented by IntensityNoiseThreshold.

By way of another embodiment, the image-processing device can implement a rule at step 210 that pertains to the signal intensity enhancement value of a voxel as compared to a signal intensity enhancement threshold. The image-processing device can utilize both a baseline signal intensity value and a late phase signal intensity value of a voxel to derive a signal intensity enhancement value for the voxel. The image-processing device can enable a user to manually set the signal intensity enhancement threshold to be utilized (e.g. 15%). In one embodiment, the logic rule takes the form of the following equation:

$$\frac{I_v(LastPhase) - I_v(FirstBaseline)}{I_v(FirstBaseline)} 100\% > EnhancementThreshold \quad (Eq. 5)$$

In Eq. 5, method 200 does not discard a voxel v if the normalized difference between the late phase signal intensity value as represented by $I_v$(LastPhase) and the baseline signal intensity value as represented by $I_v$(FirstBaseline) is greater than the signal intensity enhancement threshold represented by EnhancementThreshold.

By way of another embodiment, the image-processing device can implement a rule at step 210 that pertains to the signal intensity curve "madness" of a voxel as compared to a Smoothness threshold. The image-processing device can implement the illustrative techniques for evaluating signal intensity curve madness and setting madness thresholds are described in the applicant's above-incorporated U.S. Pat. No. 7,903,853. In an embodiment, the logic rule takes the form of the equation:

$$Curve_v > Smoothness\ Threshold \quad (Eq. 6)$$

In Eq. 6, method 200 does not discard a voxel v if the voxel's signal intensity curve madness as represented by $Curve_v$ is greater than a madness threshold represented by Smoothness Threshold.

In various embodiments, the image processing device can include the execution of all three rules at step 210 in which a voxel v is considered only a tissue voxel if it satisfies a baseline intensity rule, a signal intensity enhancement rule, and a madness rule.

Referring now to step 220 of method 200, the image-processing device calculates the average signal intensity of the tissues at each of the plurality of dynamic phases of the dataset. In one embodiment, utilizing tissue voxels derived from step 210, the image processing device performs each average signal intensity calculation according to the following equation:

$$pAveScore(t) = \sum_{v=1}^{N} (I_v(t)/N) \quad (Eq. 7)$$

In Eq. 7, t represents the dynamic phase, N represents the number of tissue voxels, and $I_v$ represents the signal intensity of a voxel v. Thus, each dynamic phase t has associated therewith a corresponding average signal intensity value (pAveScore).

Figure 3:
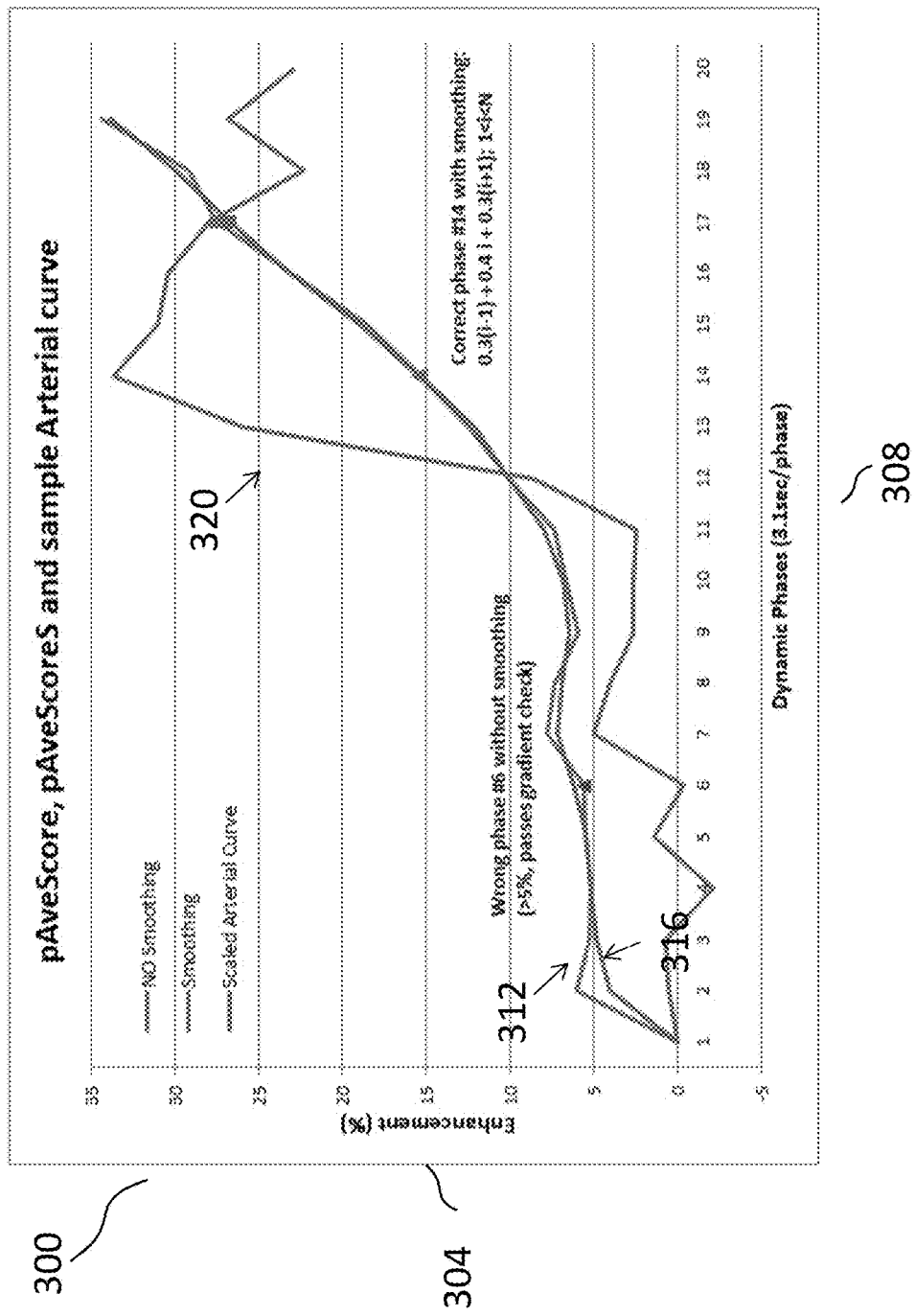
FIG. 3 is a line graph illustrating smoothed and non-smoothed average intensity enhancement curves derived from an exemplary contrast-enhanced medical image dataset.

Now referencing FIG. 3, there is shown an exemplary line graph 300 that plots a plurality of enhancement (%) values 304 over a plurality of dynamic phases 308. Enhancement values are indicative of relative changes in average signal intensity calculations pAveScore over the dynamic phases t. Line graph 300 displays this information as a series of data points connected by straight line segments to form a curve 312 (pAveScore(t)). According to one embodiment of the invention, the image-processing device can smooth curves derived from step 220 (such as curve 312), particularly if the device detects that the dataset under processing was acquired using a temporal protocol that is greater than a predefined temporal condition. In some embodiments, the image-processing device smoothes the curve if the dataset was acquired using a protocol of 15 seconds per phase (or faster). In further embodiments, the image-processing device can set and apply smoothing as a function of dataset temporal resolution information. In one embodiment of the invention, the image-processing device smoothes curves using a linear smoothing algorithm. The image-processing device can implement illustrative techniques such as an N-point window filter (Oppenheim, Alan V.; Schafer, Ronald W.; Buck, John A. (1999). *Discrete-time signal processing*. Upper Saddle River, N.J.: Prentice Hall. pp. 468-471) or a median filter (Pratt, William K. *Digital Image Processing*. 4th ed. Hoboken, N.J.: John Wiley & Sons, 2007, p. 277). In FIG. 3, there is shown a smoothed curve 316 (pAveScoreS (t)) that an image processing device derived by applying a linear smoothing algorithm to the curve 312. In this dataset, if the method applies no smoothing to the curve, the method can make an incorrect contrast arrival detection assessment (phase #6) due to the signature of the sharp, false increase in enhancement between dynamic phases 6 and 7. However, if the method applies linear smoothing, the method diminishes or moderates the false increase and makes a correct arrival detection assessment (phase #14, as indicated by a correlation with the peak of the scaled reference arterial curve 320).

Referring now to step 230 of method 200, the image processing device identifies a contrast arrival phase of the dataset. In one embodiment, the image processing device and method can identify the contrast arrival phase using features and rules designed to identify the onset of enhancement from the average signal intensity statistics calculated at step 220.

A feature of interest is the average intensity of a dynamic phase compared with the average intensities of the later dynamic phases. In some embodiments, contrast arrival detection methods described herein utilize this feature in the form of a rule. In one embodiment, the rule can take the form of:

if the average signal intensity at a dynamic phase is greater than the average intensity at any later dynamic phase, contrast arrival detection methods can eliminate the dynamic phase from consideration as the contrast arrival phase.

Another feature of interest characterizes the increase in average signal intensity at a dynamic phase over the average signal intensity of a reference baseline phase. In various embodiments, contrast arrival detection methods described herein utilize this feature in the form of a rule. By way of one embodiment, the rule can take the form of: if an increase in average signal intensity at a dynamic phase relative to the average signal intensity of a reference baseline phase does not exceed a predefined threshold, contrast arrival detection methods can eliminate the dynamic phase from consideration as the contrast arrival phase.

Another feature of interest characterizes a gradient or slope of average signal intensity change. Detection methods can employ gradient average signal intensity change features in order to avoid falsely detecting slow drifts in overall enhancement as contrast arrival. In some embodiments, contrast arrival detection methods described herein utilize the gradient feature in the form of a rule. By way of one embodiment, the rule can take the form of: if the average signal intensity curve fits under the gradient line of average signal intensity change at a dynamic phase, contrast arrival detection methods can identify the dynamic phase as the contrast arrival phase.

Figure 4A:
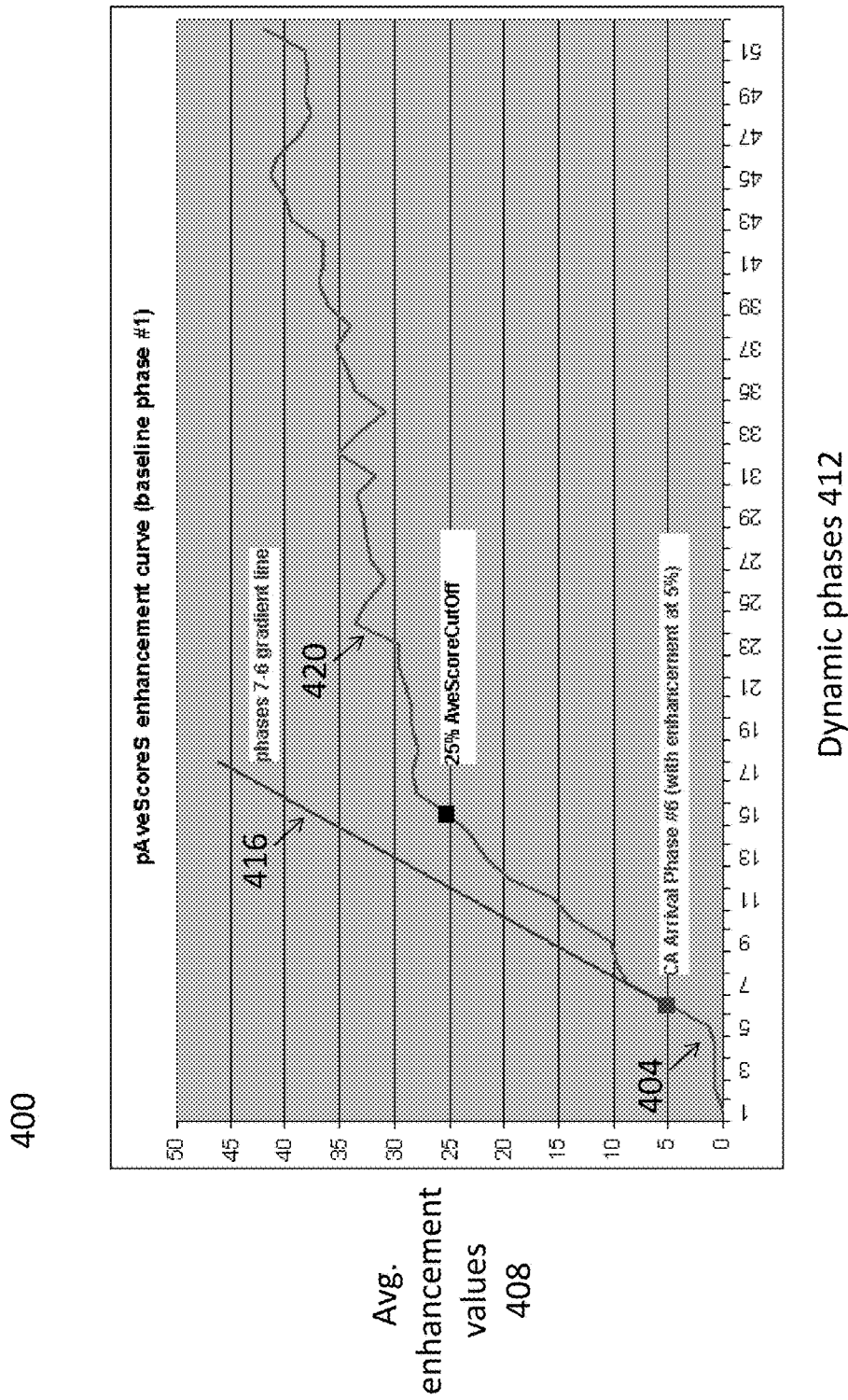
FIGS. 4A and 4B are line graphs illustrating a gradient line feature that can be utilized in accordance with embodiments of automatic contrast arrival detection procedures.

FIG. 4A is a line graph 400 illustrating an enhancement curve 404. The curve depicts the relationship between smoothed average enhancement values (pAveScoreS) 408 over a plurality of dynamic phases 412. Graph 400 indicates a gradient line 416 computed from the average signal intensity statistics of dynamic phases #6 and #7. In this runtime output example, dynamic phase #6 represents the contrast arrival phase for the dataset. An enhancement curve portion represented by the numeral 420 fits under the gradient line 416, meaning that a characterization of this feature and rule in datasets where the contrast arrival phase is unknown can assist in the automatic detection of contrast arrival phases.

Figure 4B:
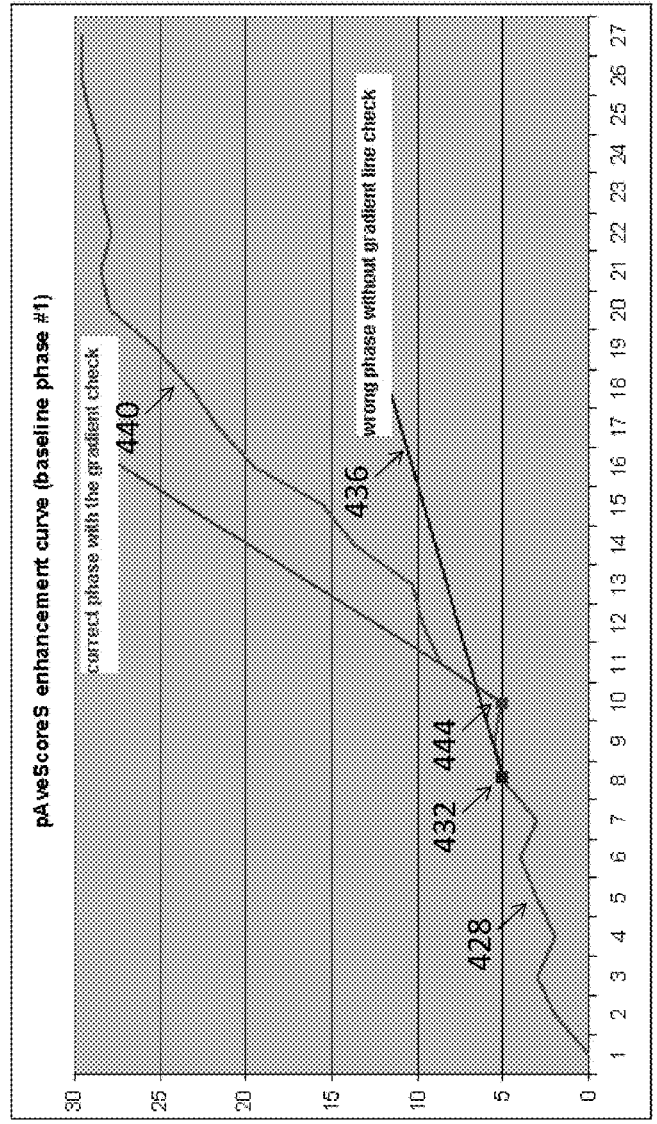

FIG. 4B is a line graph 424 illustrating an enhancement curve 428 with slow increasing signal drift during the first 10 dynamic phases. The increase in average signal intensity value here is typically not related to actual contrast injection induced enhancement. Dynamic phase #8, indicated by the numeral 432, can exhibit an increase in average signal intensity over a reference baseline phase, exceeding the predefined enhancement threshold. However, dynamic phase #8 contains a gradient line 436 that does not fit over the average signal enhancement curve portion 440, enabling contrast arrival detection methods to correctly determine that dynamic phase #8 is not a contrast arrival phase. Dynamic phase #10, indicated by the numeral 444, meets both features of interest described hereinabove.

In various embodiments, the methods described herein utilize a plurality of features and rules to detect contrast arrival phases. In one embodiment, in order for a dynamic phase to be considered a contrast arrival phase, the increase in average signal intensity at the dynamic phase relative to the average signal intensity of a reference baseline phase exceeds a predefined threshold, the average signal intensity at the dynamic phase does not exceed the average intensities at the later phases, and the average signal intensity curve must fit under the gradient of average signal intensity change at a dynamic phase. In some embodiments, the methods set the first dynamic phase of a dataset that meets all three conditions as the contrast arrival phase.

Figure 5:
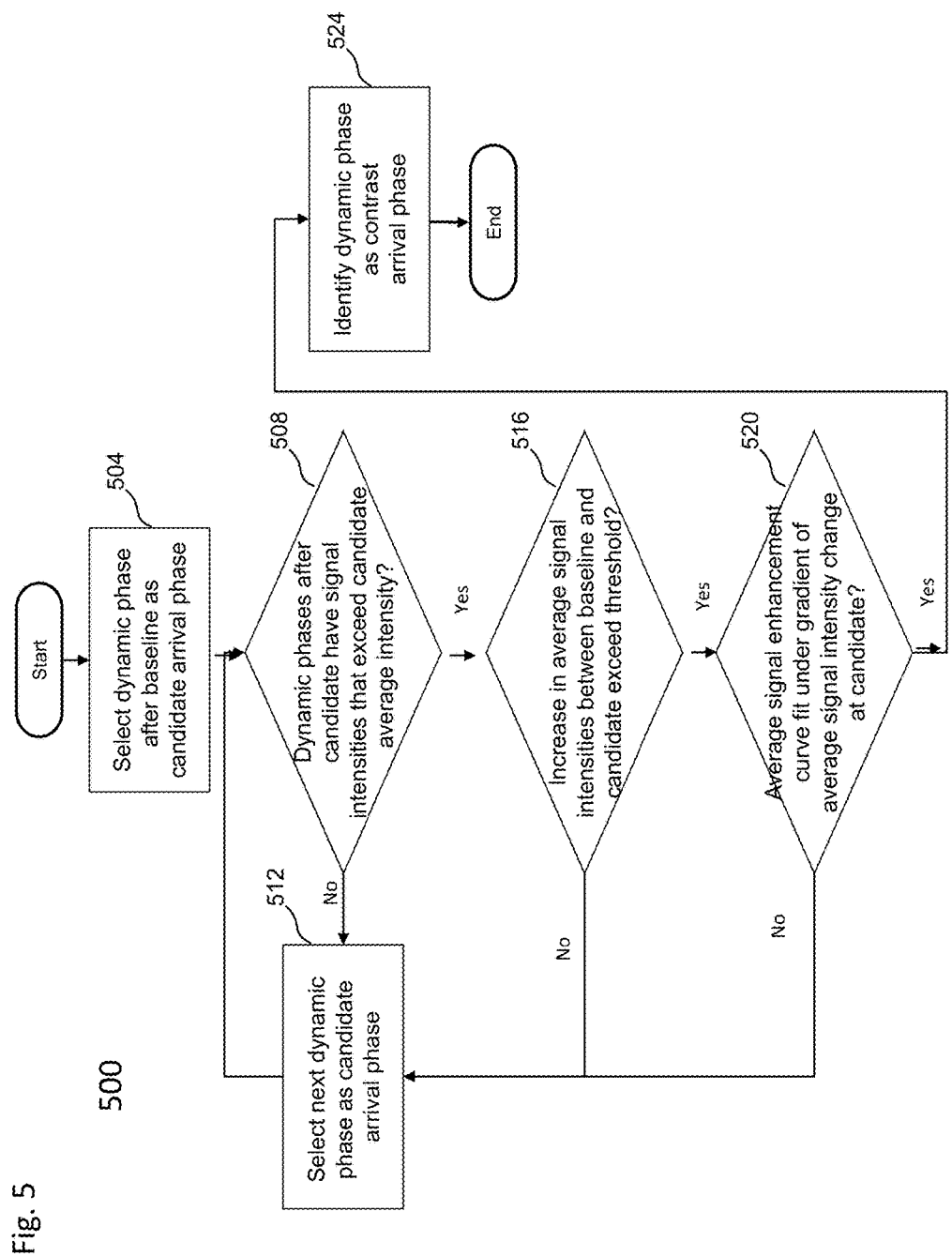
FIG. 5 is a runtime flow chart illustrating various features and rules that can be implemented as part of the illustrative, automatic contrast arrival detection procedure of FIG. 2.

FIG. 5 is a runtime flow chart shown an illustrative method 500 for identifying a contrast arrival phase using the plurality of features described herein above. At a step 504, method 500 selects a dynamic phase after a baseline phase as a first candidate arrival phase.

At an optional step 508, method 500 determines if all dynamic phases after the first candidate arrival phase have average signal intensities that exceed the average signal intensity of the first candidate arrival phase. If method 500 determines the candidate arrival phase does not meet this condition, the method proceeds to step 512 and selects the next candidate arrival phase in the dataset. If method 500 determines the candidate arrival phase meets the condition, the method proceeds to step 516.

At a step 516, method 500 determines if the increase in average signal intensity between a reference baseline phase and the first candidate arrival phase exceeds a predefined threshold. If method 500 determines the candidate arrival phase does not meet this condition, the method proceeds to step 512 to select the next candidate arrival phase in the dataset. If method 500 determines this condition is met, the method proceeds to step 520.

At a step 520, method 500 determines if the average signal intensity curve fits under the gradient of average signal intensity change at the first candidate arrival phase. If method 500 determines the candidate arrival phase does not meet this condition, the method proceeds to step 512 and selects the next candidate arrival phase in the dataset. If method 500 determines the candidate arrival phase meets the condition, method 500 proceeds to step 524 and identifies the candidate arrival phase as the actual arrival phase in the dataset.

In various embodiments, method 500 can reach a condition in which there are no additional candidate arrival phases in the dataset. Method 500 can determine any of the following conditions exist in the dataset under processing: no contrast agent injected; user-selected parameter options (e.g., noise threshold) were inadequate, or dataset includes artifacts or motion that cannot be corrected. In some embodiments, method 500 can utilize a default arrival phase or alternate methods for detection. Method 500 can notify the user to check the dataset for the presence of contrast media, artifacts and/or motion, and to potentially adjust any user-specifiable settings.

Datasets typically include a large number of dynamic phases captured after the onset of enhancement. In various embodiments, contrast arrival detection methods described herein can apply a rule designed to eliminate some of those late post-injection dynamic phases from consideration as candidate arrival phases. In an embodiment, the rule can be based on the amount of average signal intensity increase relative to a baseline average signal intensity metric. Such a rule can be implemented using the following equation:

$$AveScoreCutOff = \min(t) \text{ if } \left( \frac{pAveScoreS(t) - pAveScoreS(FirstBaseline)}{pAveScoreS(FirstBaseline)} 100\% \geq CutOffThreshold \right) \quad (\text{Eq. 8})$$

In Eq. 8, pAveScoreS(t) represents the smoothed average intensity value at dynamic phase t, pAveScoreS(FirstBaseline) represents the smoothed average intensity value at a baseline phase, and CutOffThreshold represents a user-specified percentage threshold (e.g., 25% for prostate datasets). User-specified threshold values can be based on the expected dynamic behavior of imaged tissues, given particular image acquisition settings. Hence, values can be user-specified for a particular setup. In various embodiments, the value can be greater than a user-specified per-voxel EnhancementThreshold value (see Eq. 5).

In various aspects, the contrast arrival detection methods described herein enable clinicians to image anatomical regions or tissues of interest without requiring arterial vessels to be present within the field of view. Thus, the methods can enable clinicians to image such regions or tissues with finer spatial resolutions.

Conclusion

It should be clear that the above-described system and method for automated contrast arrival detection in temporally phased images or datasets of tissues increases overall efficiency and effectiveness in diagnosis of conditions by clinicians in tissues that are partially or completely free of arterial vessels normally desired for proper imaging of contrast media arrival (thus defined as tissues that are "substantially free of arteries").

The foregoing has been a detailed description of illustrative embodiments of the invention. Various modifications and additions can be made without departing from the spirit and scope of this invention. Each of the various embodiments described above can be combined with other described embodiments in order to provide multiple features. Furthermore, while the foregoing describes a number of separate embodiments of the system and method of the present invention, what has been described herein is merely illustrative of the application of the principles described herein. For example, some or all of the processes described herein can be implemented in hardware, software, including a non-transitory computer-readable medium of program instructions. Note also, as used herein the terms "process" and/or "processor" should be taken broadly to include a variety of electronic hardware and/or software based functions and components. Moreover, a depicted process, processing board, or processor can be combined with other processes and/or processors or divided into various sub-processes or processors. Such sub-processes and/or sub-processors can be variously combined according to embodiments herein. Likewise, it is expressly contemplated that any function, process and/or processor herein can be implemented using electronic hardware, software consisting of a non-transitory computer-readable medium of program instructions, or a combination of hardware and software. Moreover, it is contemplated that some or all vision system processing tasks can be carried out either in the main module or in a remote processor (e.g. a server or PC) that is operatively connected through the interface module to the main module via a wired or wireless communication (network) link. Also, while the embodiments described herein relate generally to MR and CT-type scans, it is expressly contemplated that the teachings herein can be applied to any scanning device that generates an image of internal tissue which includes a contrast-enhancing substance (such as, but not limited to, magnetic nanoparticles and other scan-influenced substances) by those of skill in the art. Accordingly, this description is meant to be taken only by way of example, and not to otherwise limit the scope of this invention.

What is claimed is:

1. A method for automated contrast arrival detection in temporally phased images or datasets of tissues comprising:
   (a) identifying a plurality of tissue voxels in a plurality of temporally phased images as a function of voxel enhancement characteristics associated with discrete tissue voxels;
   (b) computing with a processor average enhancement characteristics from the plurality of identified tissue voxels;
   (c) comparing the average enhancement characteristics with predetermined average enhancement characteristics associated with contrast media arrival phases by operations including eliminating a current dynamic phase from consideration as the contrast arrival phase if the average signal intensity of the current dynamic phase exceeds at least one average signal intensity of a later dynamic phase relative to the current dynamic phase; and
   (d) identifying contrast media arrival phases in the temporally phased images based on the comparing.

2. The method of claim 1 further comprising, establishing a plurality of candidate arrival phases and determining if an average signal enhancement curve after the candidate phase fits under a gradient line of average signal enhancement change at a first candidate arrival phase from the plurality of candidate arrival phases, and if the average signal enhancement curve does not fit, selecting a next candidate arrival phase from the plurality of candidate arrival phases.

3. The method of claim 2 wherein, if the average signal enhancement curve fits, selecting the candidate arrival phase as one of the contrast media arrival phases in at least one of the datasets.

4. The method of claim 1 further comprising storing at least one of the contrast media arrival phases in a data storage device.

5. The method of claim 4 further comprising outputting at least one of the contrast media arrival phases to an output device.

6. The method of claim 1 wherein the tissues are substantially free of arteries.

7. The method of claim 1 wherein the identifying comprises comparing voxel enhancement values of the temporally phased images with an intensity noise threshold and identifying the plurality of tissue voxels based at least on the comparing.

8. The method of claim 1 wherein the identifying comprises comparing signal intensity enhancement voxel values of the temporally phased images with a signal intensity enhancement threshold.

9. The method of claim 1 wherein the identifying comprises comparing signal intensity madness voxel values of the temporally phased images with a smoothness threshold.

10. A system for automated contrast arrival detection in temporally phased images or datasets of tissues comprising:

(a) a set identified as a plurality of tissue voxels in a plurality of temporally phased images as a function of voxel enhancement characteristics associated with discrete tissue voxels;

(b) a process that computes, with a processor, average enhancement characteristics from the plurality of identified tissue voxels; and (c) a comparator that generates a comparison result by comparing the average enhancement characteristics with predetermined average enhancement characteristics associated with contrast media arrival phases by operations including eliminating a current dynamic phase from consideration as the contrast arrival phase if the average signal intensity of the current dynamic phase exceeds at least one average signal intensity of a later dynamic phase relative to the current dynamic phase and not eliminating the current dynamic phase from consideration as the contrast arrival phase if the average signal intensity of the current dynamic phase does not exceed at least one average signal intensity of a later dynamic phase and that identifies contrast media arrival phases in the temporally phased images based on the comparison result.

* * * * *